(12) United States Patent
Wang et al.

(10) Patent No.: US 6,616,820 B2
(45) Date of Patent: Sep. 9, 2003

(54) EXHAUST SPECIES SENSING METHOD AND DEVICE

(75) Inventors: Da Yu Wang, Troy, MI (US); Raymond L. Bloink, Swartz Creek, MI (US); Frederick L. Kennard, Holly, MI (US); Lone-Wen F. Tai, Rochester Hills, MI (US); Eric J. Detwiler, Davison, MI (US); Walter J. Symons, Grand Blanc, MI (US); Paul C. Kikuchi, Fenton, MI (US); Lora Younkman, Grand Blanc, MI (US)

(73) Assignee: Delphi Technologies, Inc., Troy, MI (US)

( * ) Notice: Subject to any disclaimer, the term of this patent is extended or adjusted under 35 U.S.C. 154(b) by 0 days.

(21) Appl. No.: 09/737,518

(22) Filed: Dec. 15, 2000

(65) Prior Publication Data

US 2002/0106306 A1 Aug. 8, 2002

(51) Int. Cl.$^7$ .......................... G01N 27/26; G01N 7/00; G01N 27/00
(52) U.S. Cl. .................... 204/411; 422/83; 422/98; 204/193; 204/410; 204/424; 204/426
(58) Field of Search ............... 422/83, 98; 204/193, 204/410, 411, 421–429

(56) References Cited

U.S. PATENT DOCUMENTS

| | | | |
|---|---|---|---|
| 4,225,410 A | * | 9/1980 | Pace .......................... 204/412 |
| 4,822,564 A | | 4/1989 | Howard |
| 4,859,307 A | * | 8/1989 | Nishizawa et al. ......... 204/425 |
| 4,905,652 A | * | 3/1990 | Nakajima et al. ........... 123/679 |
| 4,927,517 A | | 5/1990 | Mizutani et al. |
| 5,395,506 A | * | 3/1995 | Duce et al. .................. 204/426 |
| 5,486,336 A | | 1/1996 | Dalla Betta et al. |
| 5,554,269 A | * | 9/1996 | Joseph et al. ................ 204/424 |
| 5,800,783 A | | 9/1998 | Nanaumi et al. |
| 6,179,989 B1 | * | 1/2001 | Kennard, III et al. ...... 205/711 |
| 6,346,178 B1 | * | 2/2002 | Lankheet .................... 204/424 |
| 6,365,036 B1 | * | 4/2002 | Polikarpus ............... 205/784.5 |

* cited by examiner

*Primary Examiner*—Jill Warden
*Assistant Examiner*—Brian Sines
(74) *Attorney, Agent, or Firm*—Patrick M. Griffin

(57) ABSTRACT

A gas sensor for sensing $NO_x$ having electrochemical cells wherein dielectric material surrounds electrolytes except where electrodes are attached. Thereby, the exhaust gas is effectively prevented from contacting the electrolytes of the sensor's electrochemical cells. With the use of this technique, signal cross talk is minimized while enhancing NOx sensing sensitivity. Further, the total number electrodes needed are reduced which allows for more complex sensors structures.

21 Claims, 6 Drawing Sheets

EXHAUST SPECIES SENSING METHOD AND DEVICE

TECHNICAL FIELD

The present disclosure relates to exhaust gas sensors. More particularly, the present disclosure relates to an exhaust gas sensor with enhanced nitrous oxides sensing capabilities.

BACKGROUND

Exhaust sensors are used in a variety of applications that require qualitative and quantitative analysis of gases. For example, exhaust sensors have been used for many years in automotive vehicles to sense the presence of exhaust gases. In automotive applications, the direct relationship between various exhaust gas concentrations and the air-to-fuel ratios of the fuel mixture supplied to the engine allows the sensor to provide concentration measurements for determination of optimum combustion conditions, maximization of fuel economy, and the management of exhaust emissions.

Particularly with nitrogen oxides ($NO_x$), there are several different ways to detect $NO_x$ in exhaust gas. These methods are thermal, optical, electronic resistive, and electrochemical. U.S. Pat. No. 5,486,336 to Betta et al., U.S. Pat. No. 4,822,564 to Howard, U.S. Pat. No. 5,800,783 to Nanaumi et al., and U.S. Pat. No. 4,927,517 to Mizutani et al. demonstrate each of these methods of detecting $NO_x$, respectively. Among the conventional $NO_x$ detection methods, the electrochemical method has proven to be particularly effective because the sensor materials are compatible with the high temperature environment created by the exhaust gas. With the electrochemical method, there are two basic principles involved in $NO_x$ sensing: the Nernst principle and the polarographic principle.

With the Nernst principle, chemical energy is converted into electromotive force (emf). A gas sensor based upon this principle typically consists of an ionically conductive solid electrolyte material, a porous electrode on the sensor's exterior exposed to the exhaust gases with a porous protective overcoat, and a porous electrode on the sensor's interior surface exposed to the partial pressure of a known gas. Sensors typically used in automotive applications use a yttria stabilized zirconia based electrochemical galvanic cell with porous platinum electrodes, operating in potentiometric mode, to detect the relative amounts of a particular gas, such as oxygen for example, that is present in an automobile engine's exhaust. This is particularly relevant as $NO_x$ sensors catalytically reduce $NO_x$ to nitrogen gas and oxygen, wherein the liberated oxygen is then measured. When opposite surfaces of the galvanic cell are exposed to different oxygen partial pressures, an electromotive force is developed between the electrodes on the opposite surfaces of the zirconia wall, according to the Nernst equation:

$$E = \left(\frac{-RT}{4F}\right)\ln\left(\frac{P_{O_2}^{ref}}{P_{O_2}}\right)$$

where:

-continued $E$ = electromotive force (emf)
$R$ = universal gas constant
$F$ = Faraday constant
$T$ = absolute temperature of the gas
$P_{O_2}^{ref}$ = oxygen partial pressure of the reference gas
$P_{O_2}$ = oxygen partial pressure of the exhaust gas With the polarographic principle, the sensors utilize electrolysis; that is, by measuring the current required to decompose a gas, such as $NO_x$, the concentration of that gas can be determined. Generally, this type of sensor is composed of a pair of current pumping electrodes where both are in contact with an oxide conductive solid electrolyte and one electrode is in contact with a gas diffusion limiting medium. The gas diffusion limiting means in conjunction with the pump electrode creates a limiting current which is linearly proportional to the measured gas concentration in the sample.

For example, one known type of exhaust sensor includes a flat plate sensor formed of various layers of ceramic and electrolyte materials laminated and sintered together with electrical circuit and sensor traces placed between the layers in a known manner. Within the sensor, a flat plate sensing element is employed. This sensing element can be both difficult and expensive to package within the body of the exhaust sensor since it generally has one dimension that is very thin and is usually made of brittle materials. Consequently, great care and time consuming effort must be taken to prevent the flat plate sensing element from being damaged by exhaust, heat, impact, vibration, the environment, etc. This is particularly problematic since most materials conventionally used as sensing element supports, for example, glass and ceramics, cannot withstand much bending. After the sensor is formed, exhaust gas can be sensed.

Particular to $NO_x$ sensors, treatment of the exhaust gas is employed prior to being analyzed utilizing the Nernst and/or polarographic principles. Typically, this is achieved using catalyst and/or by maintaining the other gasses at constant levels within an enclosed or semi-enclosed environment. Once the exhaust is treated, the gas encounters the sensor's electrochemical cells.

A typical prior art $NO_x$ sensor will have two electrochemical cells. The first cell has an exhaust gas diffusion limiting means, two oxygen pumping electrodes, and two oxygen sensing electrodes separated by an oxide conducting solid electrolyte. The second cell has a gas diffusion limiting means that connects to the first cell, two pumping electrodes, two sensing electrodes, and an oxide conducting solid electrolyte between the electrodes. The first cell has one pumping electrode exposed to ambient exhaust gas and the other pumping electrode exposed to the inside of the first cell. As to the first cell's sensing electrodes, one is exposed to a reference gas while the other is located within an interior portion of the first cell. The pumping electrodes of the second cell have one electrode exposed to exhaust gas and the other electrode exposed to the interior of the second cell. As with the first cell, the second cell has one sensing electrode exposed to a gas and the other exposed to the interior of the second cell. In use, the electrodes located inside the first cell have substantially no effect on the $NO_x$ concentration so that only the oxygen concentration is modulated and not the $NO_x$ concentration. The electrodes inside the second cell have an effect on the $NO_x$ concentration via using a catalyst. Thereby, $NO_x$ sensing can be achieved with either the Nernst and/or the polarographic principles. Generally, a heater is provided to maintain a constant operating temperature within the sensor.

As such, existing electrochemical $NO_x$ sensors employ multiple electrochemical cells that share a common oxide conducting solid electrolyte. These cells have a frequent tendency to electrically cross-communicate and interfere with each other. Accordingly, there remains a need in the art for a $NO_x$ sensor having minimal cross-communication and interference between sensor electrochemical cells.

SUMMARY

The deficiencies of the above-discussed prior art are overcome or alleviated by the gas sensor and method of making the same. One embodiment of the gas sensor comprises: a first electrochemical cell having a first electrolyte disposed between and in ionic communication with first and second electrodes; a second electrochemical cell having a second electrolyte disposed between and in ionic communication with third and fourth electrodes wherein said first and second electrochemical cells are ionically isolated from each other; and a third electrochemical cell having a fifth electrode disposed on the same side of the second electrolyte as the third electrode. The fifth electrode and third electrode are arranged to be disposed in a spaced relation. Additionally, the first and second electrolytes are each disposed in a separate layers of dielectric material.

In another embodiment, the gas sensor, comprises: a first electrochemical cell having a first electrolyte disposed between and in ionic communication with first and second electrodes; a second electrochemical cell having a second electrolyte disposed between and in ionic communication with third and fourth electrodes wherein said first and second electrochemical cells are ionically isolated from each other; a third electrochemical cell having a fifth electrode disposed on the same side of the second electrolyte as the third electrode, wherein the third and fifth electrodes are disposed in a spaced relation; and a fourth electrochemical cell disposed on a side of the second electrochemical cell opposite the first electrochemical cell, the fourth electrochemical cell having a third electrolyte disposed between and in ionic communication with sixth and seventh electrodes, wherein the fourth electrochemical cell is disposed in a dielectric layer, and wherein the first, second, and fourth electrochemical cells substantially ionically isolated from one another. The first and second electrolytes are each disposed in a separate layers of dielectric material.

Alternatively to avoid electrical cross-communication and interference between electrochemical cells using a shared electrolyte, a dielectric insulation layer is inserted between the two electrochemical cells. Or to avoid electrical cross-communication and interference between electrochemical cells, the cells arrangement involve both of the two schemes mentioned above.

BRIEF DESCRIPTION OF THE DRAWINGS

Referring now to the drawings wherein like elements are numbered alike in the several Figures.

DETAILED DESCRIPTION OF INVENTION

Figure 1:
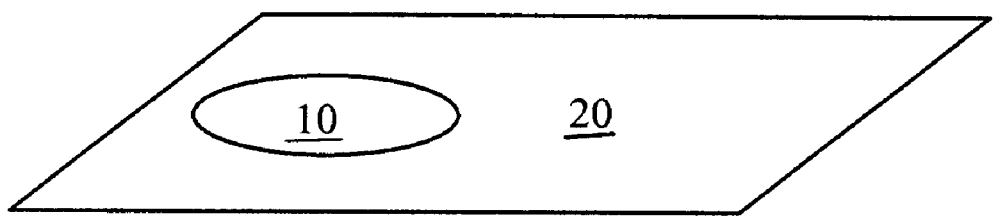
FIG. 1 is a perspective layout view of a dielectric material and electrolyte prior to the electrolyte's placement within dielectric material.

A $NO_x$ sensor is similar to other gas sensors, particularly oxygen sensor, in that both Nernst and current-pumping type electrochemical cells can be utilized. As stated above, sensors typically contain multiple electrochemical cells that share an oxide conducting solid electrolyte. To avoid electrical cross-communication and interference between electrochemical cells, an electrolyte preferably is embedded in dielectric material. By embedding the electrolyte in dielectric material and between electrodes, the electrolytes of the two cells avoids direct contact with each other. Alternatively, to avoid electrical cross-communication and interference between electrochemical cells using a shared electrolyte, the sensor can have a dielectric insulation layer inserted between the two electrolyte layers of the two electrochemical cells. In another alternative, the sensor can have the cells arranged in a way to involve both of the two schemes just mentioned above.

Typically in use with a $NO_x$ sensor, at least one electrochemical cell is provided as an oxygen pumping cell. The cell is positioned beneath a coating layer for poison protection from exhaust gas. The electrode facing the coating layer is typically comprises of a precious metal, such as palladium (Pd), rhodium (Ru), platinum (Pt), and the like, as well as combinations and alloys comprising at least one of the forgoing. The electrode facing an interior portion of the sensor is also typically comprised of a metal such as gold (Au) alloyed with palladium (Pd), rhodium (Ru), platinum (Pt), osmium (Os), ruthenium (Ru), iridium (Ir), zirconium (Zr), yttrium (Y), cerium (Ce), calcium (Ca), aluminum (Al), and the like, as well as other similar alloys, oxides, which have less electrochemical pumping effect on NOx, and combinations comprising at least one of the foregoing metals. By applying a current, oxygen ions can be conducted out of the interior portion of the cell. Thereby, the relative concentration of $NO_x$ is much greater than the oxygen concentration.

Used in conjunction with the oxygen pumping cell is an exhaust gas oxygen sensing cell(s) which use the Nernst principle to create an emf across an electrolyte. Typically, the electrodes comprise a precious metal, with platinum preferred for the reference electrode and platinum or platinum alloy (such as PT/Rh alloy) preferred for the sensing electrode facing the interior portion of the sensor. The reference electrode faces a reference gas while the sensing electrode faces the gas within the sensor being sampled. This difference in oxygen concentration will generate an emf that can be analyzed and compared to determine the oxygen concentration within the gas being analyzed. Depending on this determination, a process control device can operate the above mentioned oxygen pumping cell to remove additional oxygen from the sensing gas so that the $NO_x$ concentration can be easily determined.

The $NO_x$ is then determined by the $NO_x$ cell which has one electrode facing the sensing gas that has the ability to reduce $NO_x$ to nitrogen and oxygen. This is attained by using rhodium, rhodium alloy (such as a rhodium/platinum alloy), or other $NO_x$ catalyst in the electrode facing the sensing gas. By reducing the $NO_x$, the oxygen can then either be sensed using emf comparison or determined using oxygen pumping by analyzing the amount of current required to conduct the oxygen created out of the sensor.

Figure 2:
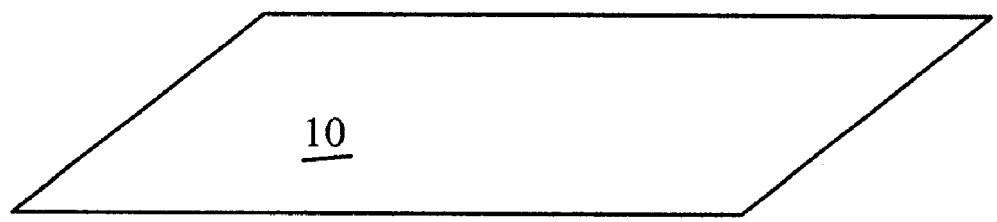
FIG. 2 is a perspective layout view of a dielectric material and electrolyte prior to the electrolyte layer being joined with a dielectric layer.
Figure 2:
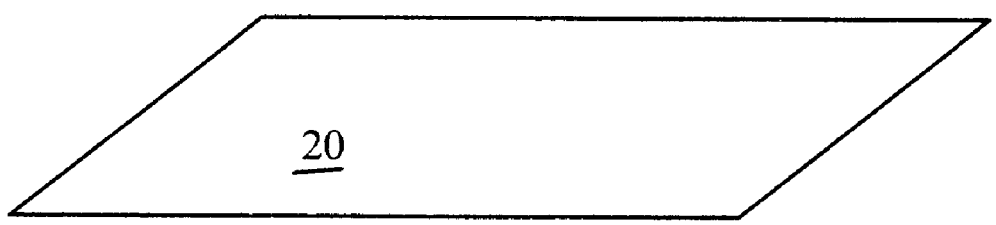

Referring now to FIG. 1, an electrolyte 10 is shown prior to being embedded in a dielectric material 20. While electrolyte 10 is depicted as a disc shaped object, any shape that will lead to a functioning sensor structure is possible, for example a circular, elliptical, rectangular, multi-sided, or the like. Referring now to FIG. 2, an electrolyte 10 layer is shown with a dielectric material 20 layer. Electrolyte 10 and dielectric material 20 are typically manufactured as tapes (sheets of rolled material). In one method of manufacturing, tapes of electrolyte 10 and dielectric material 20 are punched so that a punched disc of electrolyte 10 will fit within a corresponding punched opening in dielectric 20.

Advantageously, the materials for electrolyte 10 and dielectric 20 are selected to have similar shrinkage and thermal coefficient factors, preferably within about 5%, during manufacturing firing stage (the process of maturing ceramic products by the application of heat) and similar thermal coefficients after firing. This can be achieved with the use of doping or other additives added to the starting materials. To form tapes of the electrolyte 10 and dielectric material 20, any known method of manufacturing can be used such as roll compaction, tape casting, slip casting, or calendaring, for example. Possible electrolyte materials include any material conventionally employed as sensor electrolytes, including, but not limited to, zirconia which may optionally be stabilized with calcium, barium, yttrium, aluminum, lanthanum, cesium, gadolinium, and the like, as well as alloys, oxides, and combinations comprising at least one of the foregoing. For example, the electrolyte can be alumina and yttrium stabilized zirconia. Typically, the electrolyte has a thickness of up to about 500 microns, with a thickness of approximately 100 microns to about 250 microns preferred. Possible dielectric materials include alumina or another dielectric material capable of inhibiting electrical communication and providing physical protection. The dielectric materials can be up to about 500 microns thick, with a thickness of about 100 to about 250 microns preferred.

The electrolytes 10 can be solid or porous. Porous electrolyte should be capable of permitting the physical migration of exhaust gas and the electrochemical movement of oxygen ions, and should be compatible with the environment in which sensor is utilized. Typically, porous electrolyte has a porosity of up to about 20%, with a median pore size of up to about 0.5 microns, or, alternatively, comprises a solid electrolyte having one or more holes, slits, or apertures therein, so as to enable the physical passage of exhaust gases. Commonly assigned U.S. Pat. No. 5,762,737 to Bloink et al., which is hereby incorporated in its entirety by reference, further describes porous electrolytes that may be useful in the instant application.

Figure 3:
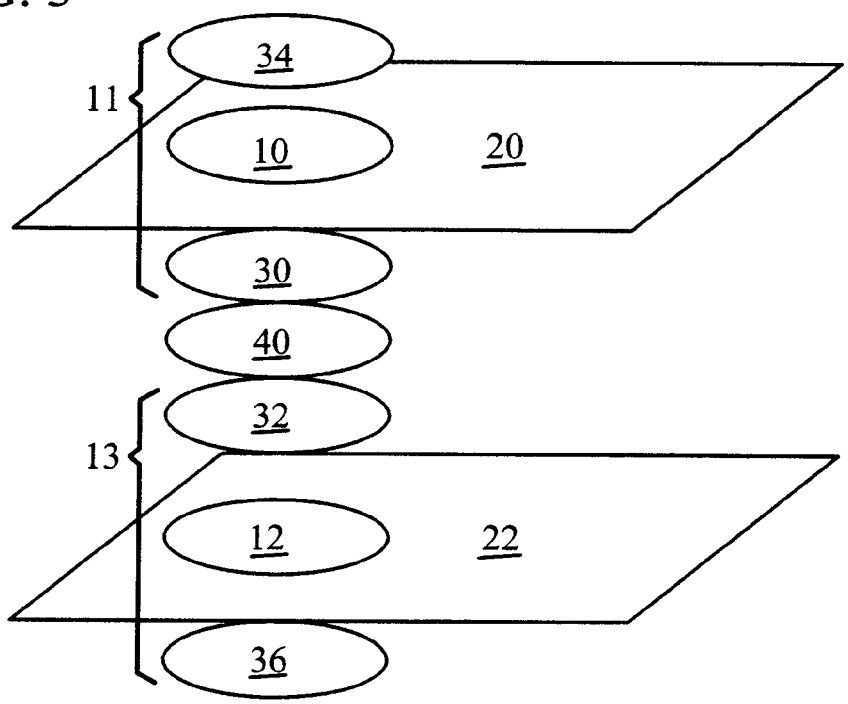
FIG. 3 is an exploded view of a portion of a $NO_x$ sensor employing the placement of electrolyte within dielectric.

Referring to FIG. 3, an exploded view showing a structure wherein electrolytes 10 and 12 are fitted within corresponding openings in dielectric materials 20 and 22, respectively. The subassembly of electrolyte 10 and dielectric material 20 is positioned adjacent to and in agreement with the subassembly of electrolyte 12 and dielectric 22. Disposed on opposite sides of electrolyte 10, are electrode 34 and electrode 30, to form a first electrochemical cell 11. Disposed on opposite sides of electrolyte 12, are electrode 32 and electrode 36, to form a second electrochemical cell 13. Electrodes 30 and 32 are positioned between electrolytes 10 and 12, with an electrode gap 40, if desired, disposed there between.

To form the electrode gap 40 (an open gas space), during sensor production, a fugitive material (e.g., a carbon based material) is positioned between electrodes 30 and 32. Upon formation, the fugitive material will burn off leaving electrode gap 40 between electrodes 30 and 32. When the fugitive material is burned off, the first electrochemical cell 11 having electrode 30 will be separate and ionically isolated from the second electrochemical cell having electrode 32.

In operation, the electrode gap 40 is in fluid communication with the gas to be sensed either via a channel or through the first electrochemical cell 11. The first electrochemical cell 11 is used as an oxygen pumping cell to pump oxygen out from the electrode gap. The second electrochemical cell 13 can then be used as a $NO_x$ sensing or oxygen cell to determine the concentration of $NO_x$ or oxygen. Alternatively, a design can be created wherein electrodes 30 and 32 are shared by the top and bottom electrochemical cells and still maintain an ionic isolation (not depicted). To achieve this, electrodes 30 and 32 can be joined together in another part of the sensor, or electrode gap 40 can be eliminated whereby electrodes 30 and 32 can be combined into one electrode. If electrodes 30 and 32 are combined, the electrode ink (electrode coating) preferably should not contain any oxide electrolytic materials.

Figure 4:
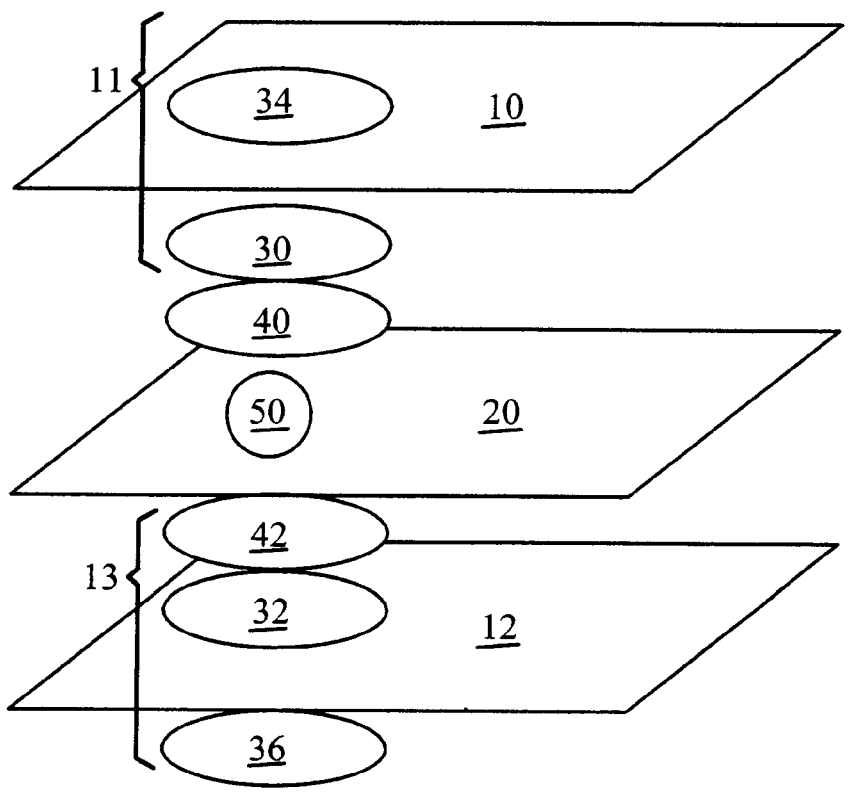
FIG. 4 is an exploded view of a portion of a $NO_x$ sensor employing a dielectric layer under the electrolyte layer.

Referring to FIG. 4, an exploded view showing a structure wherein electrolytes 10 and 12 are separated by a dielectric material layer 20. Disposed on opposite sides of electrolyte 10, are electrode 34 and electrode 30, is forming a first electrochemical cell 11. Disposed on opposite sides of electrolyte 12, are electrode 32 and electrode 36, forming a second electrochemical cell 13. Electrodes 30 and 32 are positioned between electrolytes 10 and 12 wherein electrode gap 40 and 42 are disposed in between and separated by the dielectric layer 20. To form the electrode gap 40 and 42 (an open gas space), during sensor production, a fugitive material (e.g., a carbon based material) is positioned between electrodes 30 and 32. Upon formation, the fugitive material will burn off leaving electrode gap 40 and 42 between electrodes 30, 32 and the dielectric layer 20. There is a hole or aperture 50 on dielectric layer 20 to allow fluid communication between the electrode 30 and 32.

FIGS. 5–10, various embodiments of $NO_x$ sensors employing structures based on those explained above in FIGS. 1–4.

Figure 5:
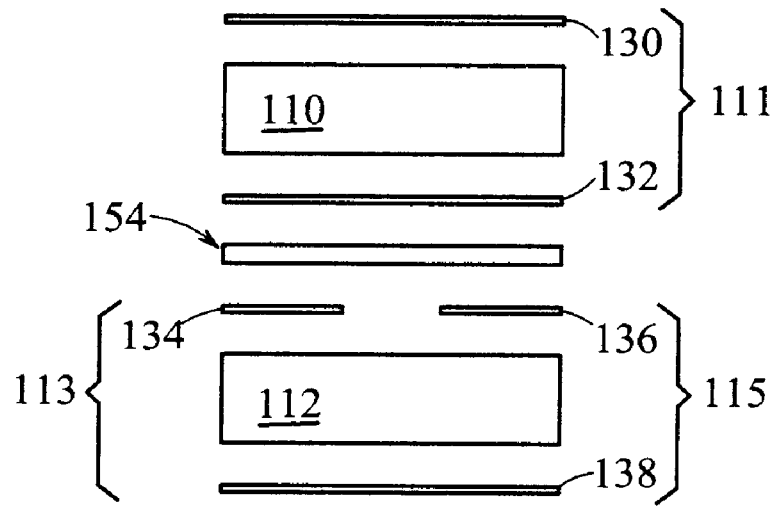
FIG. 5 is a perspective view of an example arrangement of a $NO_x$ sensor wherein two of the electrochemical cells with an embedded layout.

Referring to FIG. 5 comprising three electrochemical cells with two of these cells sharing the same electrolyte, a first electrochemical cell 111 comprises an electrolyte 110 and electrodes 130 and 132. Electrodes 130 and 132 are oxygen pumping electrodes that are in electrical communication with electrolyte 110. For example, electrode 130 can comprise platinum (Pt) and electrode 132 can comprise a gold (Au)/platinum alloy. Further, gas diffusion control is provided by a coating layer, the electrolyte (porous electrolyte or aperture(s) through the electrolyte), or by an aperture inserted between electrolytes 110 and 112. In other words, the gas to be sensed can enter the sensor and contact electrode 132 by traveling through electrolyte 110 or by passing through an aperture or passageway (not shown) disposed from electrode 132 to the exterior of the sensor.

The remaining electrochemical cells are an oxygen sensing cell and a $NO_x$ sensing cell. The second electrochemical cell 113, used for oxygen sensing, comprises electrolyte 112 and electrodes 134 and 138. The third electrochemical cell 115 used for $NO_x$ sensing, comprises sensing electrode 136, electrolyte 112, and the reference electrode 138. Reference electrode 138 is maintained in fluid communication with a reference gas source, such as oxygen or air; e.g., reference gas can be provided by oxygen pumping and an oxygen chamber, and/or with the use of an air channel connected to ambient air.

When gas, e.g., exhaust gas, enters the sensor and contacts electrode 132, the first electrochemical cell 111 acts as an oxygen pumping cell, which, upon application of current, removes the oxygen between electrodes 132 and 134. Using reference electrode 138 and sensing electrode 134 and the first electrochemical cell 111, the oxygen concentration in the area of electrodes 132, 134, and 136 is controlled at a constant value so that $NO_x$ concentration can be determined.

One method of determining the $NO_x$ concentration is by measuring the $NO_x$ emf in proximity with $NO_x$ sensing electrode 136, which is attributable to the decomposition of $NO_x$ in addition to residual oxygen content, and by measuring the oxygen emf in proximity with oxygen sensing electrode 134. Another method of determining the $NO_x$ concentration is by pumping the oxygen, which is attributable to the decomposition of $NO_x$ in addition to residual oxygen content, through electrode 136 to electrode 138. By measuring this pumping current and comparing to a current developed between electrodes 134 and 138, the concentration of $NO_x$ can be determined. Alternatively, gap 154, which can be formed from fugitive material which is burn off during firing, can be partially eliminated and electrodes 132 and 134 can be joined together to allow electronic conductance between the electrodes 132 and 134. In use, an electronic control circuit operates the sensor in determining the amount of current to be applied.

Figure 6:
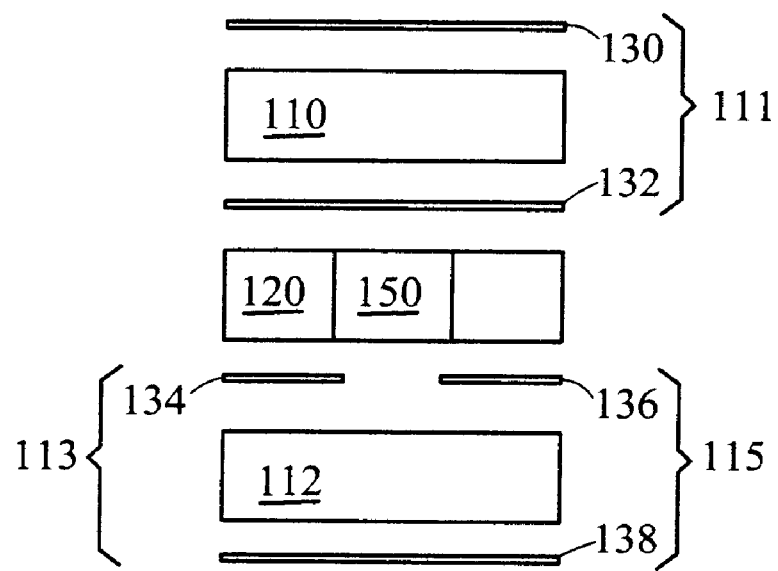
FIG. 6 is a perspective view of an example arrangement of a $NO_x$ sensor wherein two of the electrochemical cells with a layered layout.

In FIG. 6, there is a dielectric layer 120 inserted between the electrolyte layers 110 and 112. Disposed in dielectric layer 120 is preferably a hole or an aperture 150 which allows gas communicated between electrodes 132, 134, and 136.

Figure 7:
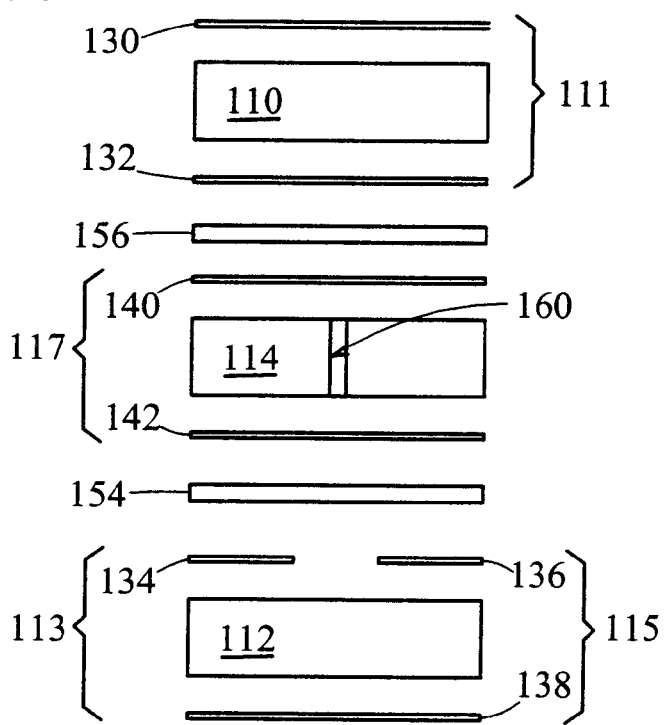
FIG. 7 is a perspective view of an example arrangement of a NOx sensor that is similar to FIG. 5 except an additional electrolyte is employed with all the cells in an embedded layout.

Referring to FIG. 7, which is similar to FIG. 5 with an additional electrochemical cell 117. This fourth electrochemical cell 117 comprises electrolyte 114 and electrodes 140 and 142 and is situated between the first and second electrochemical cells 111, 113. Electrolyte 114 can be a porous electrolyte, or a solid electrolyte comprising a hole, optionally has an aperture or the like, 160 and/or porosity control material to control the amount of $NO_x$ and any other residual gas entering contact with electrodes 134, 138, and 142. Electrodes 140 and 142 can be used as either pumping or sensing electrodes for improved removal of oxygen and improved control of the oxygen pumping cells. With this additional electrochemical cell, additional oxygen reduction can be achieved in relation to the $NO_x$ concentration. Also, due to the use of the embedded electrolytes 110, 112, 114 and/or layered electrolytes with dielectric material gaps 154, 156, cross-talk between the electrolytes is reduced verses conventional systems. Actually, the crosstalk is essentially eliminated.

Figure 8:
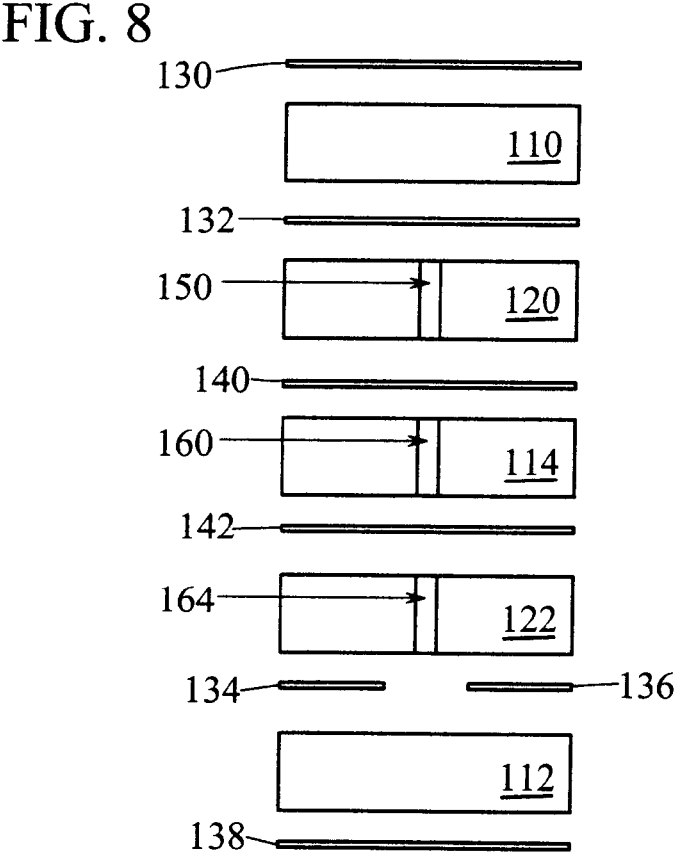
FIG. 8 is a perspective view of an example arrangement of a NOx sensor that is similar to FIG. 7 except an additional electrolyte is employed a layered layout.

In FIG. 8, the sensor has layered structure (as opposed to FIG. 7's embedded structure) with dielectric insulation layers 120 and 122 inserted between the electrolyte layers of 110, 112, and 114. Apertures or holes of 150, 164 and 160 are created on dielectric layers 120, 122 and electrolyte layer 114 so that fluid gas communication can be achieved between electrodes 132, 140, 142, 134, and 136. As with FIG. 9, electrolyte 114 can comprise a hole or aperture 160 to allow passage of exhaust gas to electrode 142. Note, if electrolyte 114 is porous, aperture 160 is not needed.

Figure 9:
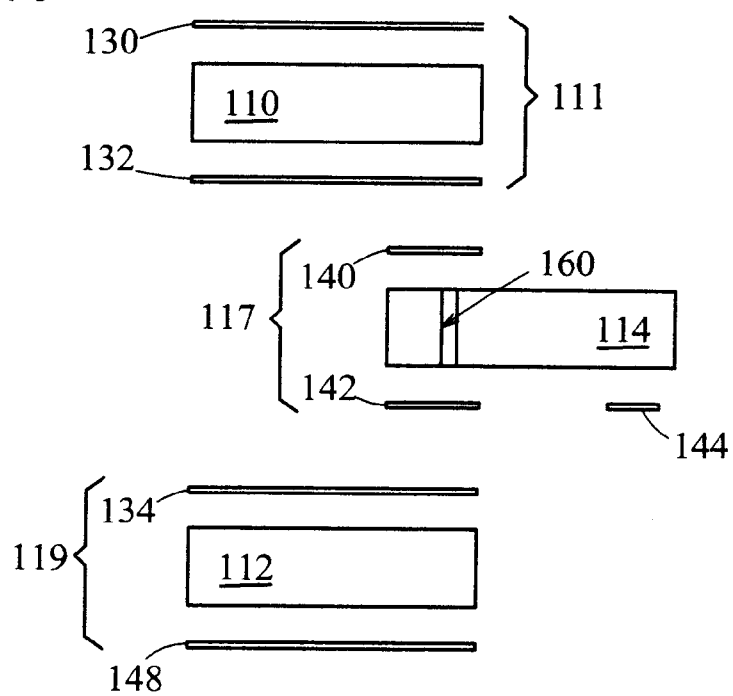
FIG. 9 is a perspective view of an example arrangement of a $NO_x$ sensor that is similar to FIG. 7 with an embedded layout for all of the cells.

Another setup is shown in FIG. 9. This setup is similar to FIG. 7 except that the forth (middle) cell 117 recesses to one side (is askew) so that reference electrode 144 can be disposed on the third cell 117, adjacent but electrically separated from electrode 142, as opposed to the second cell 119, allowing for cell isolation. The reference electrode 144 can be oxygen pumping or can have a reference (e.g., vent, reference gas storage chamber and/or material, and the like, as well as combinations comprising at least one of the forgoing references) vent connected to ambient air (not shown). With this sensor, electrode 148 is exposed to exhaust through an aperture pores, or the like, that is opened between electrode 148 and a dielectric layer (not shown) disposed on a side of the electrode 148 opposite electrolyte 112. In this arrangement, during operation, both sides of the sensor have direct access to the exhaust gas, e.g., electrodes 130 and 148 , with the air reference being electrode 144. In such an arrangement, electrolytes 110 can be solid or porous, with a solid electrolyte 112 and 114 preferred. For example, FIG. 10 illustrates a layered structure version of FIG. 9 with dielectric layers 120 and 122 inserted between electrolyte layers 110, 114 and 112.

Figure 10:
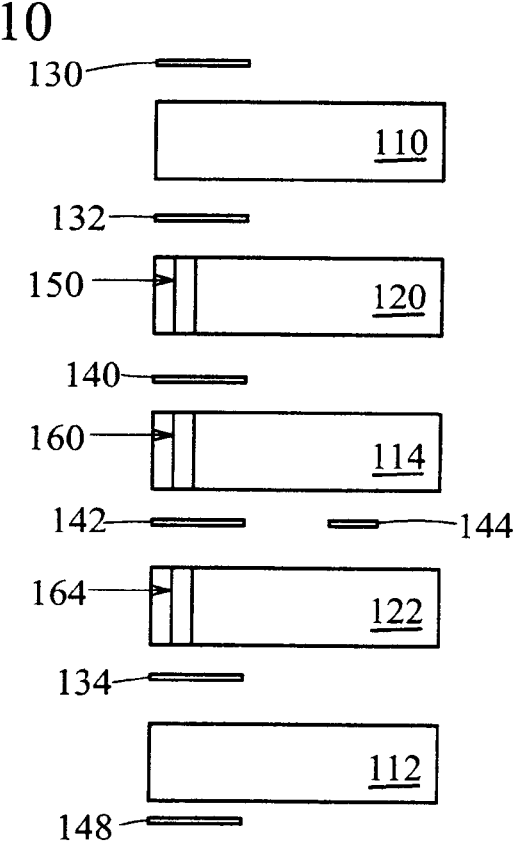
FIG. 10 is a perspective view of an example arrangement of a $NO_x$ sensor that is similar to FIG. 9 with a layered layout for all of the cells.

With the arrangement of FIGS. 9 and 10, several different modes of sensor operation are possible. Depending upon which mode of operation is selected, different electrodes can be shared. For example, sensing electrode 140 and reference electrode 144 can be arranged to control the pump electrodes 130 and 132 of the first electrochemical cell 111. Thereby, the oxygen pumping activity can be maintained at a constant level in the area around electrodes 132, 140, 142, and 134. Electrodes 134 and 148 can be then utilized as $NO_x$ pumping or sensing electrodes for the determination of the $NO_x$ concentration.

Figure 11:
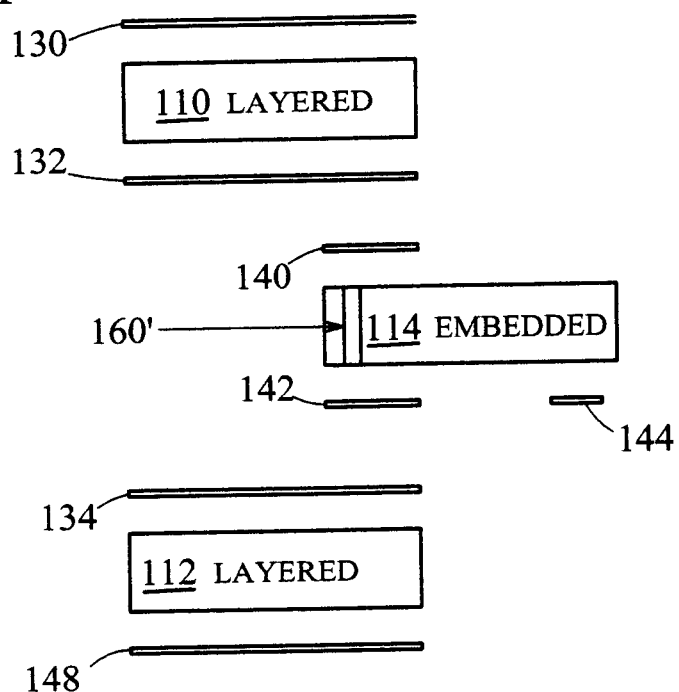
FIG. 11 is a perspective view of an example arrangement of a $NO_x$ sensor that is similar to FIG. 9 except that mixed structure are used layered structures mixed with an embedded structure.
Figure 12:
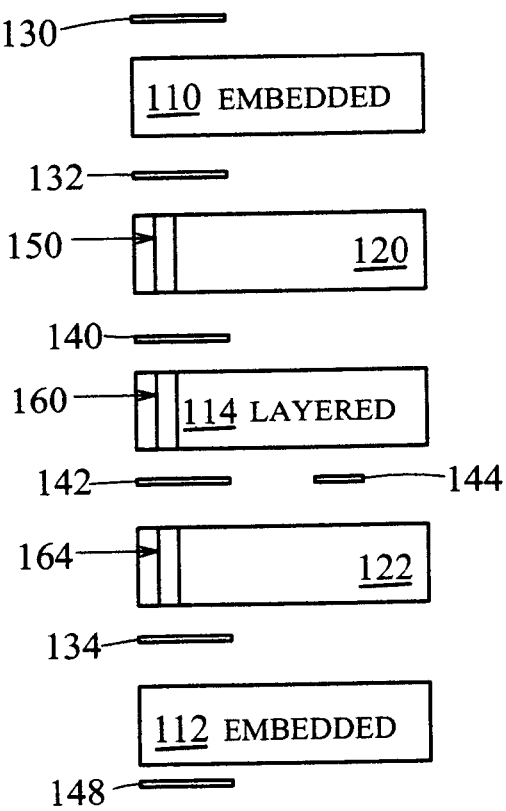
FIG. 12 is a perspective view of an example arrangement of a $NO_x$ sensor that is similar to FIG. 10 except that mixed structure used embedded structures mixed with layered structure.

Referring to FIGS. 11 and 12, a mixed structure views of the sensor depicted in FIGS. 9 and 10 are shown. As displayed in FIG. 11, the two electrolyte layers 110' and 112' are separated by a dielectric insulation layer which also has an electrolyte disk 114' inserted. In FIG. 12 the electrolyte 114" is a layer structure while electrolyte 110" and 112" are embedded structure.

In FIGS. 1–12, we did not show heaters, poison resistive coating layers, air reference channels, exhaust gas diffusion limiting means, channels to the ambient exhaust gas. These items can be easily incorporated into the sensor layouts shown in FIGS. 1–12, as the dielectric layers are used in either embedded or layered structures.

The $NO_x$ sensor arrangement avoids the cross talk and interference associated with having multiple cells sharing the same leaders that connect to the electronic controller and sensing signal reading electronics. As stated, this is achieved with the placement of the electrolyte within a corresponding opening within a dielectric strip, or with dielectric layer inserted between the electrolyte layers. The dielectric materials, such as alumina, have a high electrical resistivity and dielectric brake down voltage, which provide ionic and electronic isolation between the electrochemical cells (basically, the dielectric layer, used at 800° C. and under a 30 second duration of a 10 volt pulse applied to a 1.0 square centimeter ($cm^2$) electrode area, will generate a leakage current of about 2.8 nano-ampere (nA) to about 4.2 nA.) With these sensor arrangements, improved $NO_x$ sensing and sensor operation is obtained.

While preferred embodiments have been shown and described, various modifications and substitutions may be made thereto without departing from the spirit and scope of the invention. Accordingly, it is to be understood that the apparatus and method have been described by way of illustration only, and such illustrations and embodiments as have been disclosed herein are not to be construed as limiting to the claims.

What is claimed is:

1. A gas sensor, comprising:
   a first electrochemical cell having a first electrolyte disposed between and in ionic communication with first and second electrodes;
   a second electrochemical cell having a second electrolyte disposed between and in ionic communication with third and fourth electrodes wherein said first and second electrochemical cells are ionically isolated from each other;
   a third electrochemical cell having a fifth electrode disposed on the same side of the second electrolyte as the third electrode, wherein the fifth electrode and the third electrode are disposed in a spaced relation; and
   at least two layers of dielectric material, wherein said first and second electrolytes are each disposed in a separate layer of the dielectric material.

2. The gas sensor of claim 1, further comprising an open gas space between said second electrode and said third electrode.

3. The gas sensor of claim 1, further comprising a fourth electrochemical cell disposed on a side of the second electrochemical cell opposite the first electrochemical cell, the fourth electrochemical cell having a third electrolyte between and in ionic communication with a sixth and seventh electrode, wherein the first, second, and fourth electrochemical cells are substantially ionically isolated from one another.

4. The gas sensor of claim 3, wherein the second electrolyte comprises a fluid passageway selected from the group consisting of pores, apertures, holes, and combinations comprising at least one of the foregoing passageways.

5. The gas sensor of claim 3, wherein the second electrochemical cell is disposed askew such that the fourth and second electrodes are in fluid communication and the fifth electrode is electronically separated from the third and sixth electrodes.

6. The gas sensor of claim 5, wherein the fifth electrode is disposed in fluid communication with a reference selected from the group consisting of a vent, reference gas storage material, reference gas storage chamber, and combinations comprising at least one of the foregoing references.

7. The gas sensor of claim 5, wherein the first and seventh electrodes can fluidly communicate with an environment outside of the sensor.

8. The gas sensor of claim 1, further comprising a fourth electrochemical cell disposed between the first and second electrochemical cells, the forth electrochemical cell having a third electrolyte between and in ionic communication with sixth and seventh electrodes, wherein the first, second, and fourth electrochemical cells are substantially ionically isolated from one another.

9. The gas sensor of claim 8, wherein the third electrolyte further comprises a fluid passageway selected from the group consisting of pores, apertures, holes, and combinations comprising at least one of the foregoing passageways.

10. The gas sensor of claim 8, wherein the third electrolyte is embedded within a separate layer of dielectric material.

11. The gas sensor of claim 10, wherein the sixth and the third electrodes are disposed in a spaced relation.

12. The gas sensor of claim 8, further comprising a first insulation layer disposed between the first and fourth electrochemical cells, and a second insulation layer disposed between the fourth and the second electrochemical cells.

13. The gas sensor of claim 12, wherein the first and second insulative layers individually further comprise a fluid passage way selected from the group consisting of pores, apertures, holes, and combinations comprising at least one of the foregoing passageways.

14. A gas sensor, comprising:
    a first electrochemical cell having a first electrolyte disposed between and in ionic communication with first and second electrodes;
    a second electrochemical cell having a second electrolyte disposed between and in ionic communication with third and fourth electrodes wherein said first and second electrochemical cells are ionically isolated from each other;
    a third electrochemical cell having a fifth electrode disposed on the same side of the second electrolyte as the third electrode, wherein the third and fifth electrodes are disposed in a spaced relation;
    a fourth electrochemical cell disposed on a side of the second electrochemical cell opposite the first electrochemical cell, the fourth electrochemical cell having a third electrolyte disposed between and in ionic communication with sixth and seventh electrodes, wherein the fourth electrochemical cell is disposed in a dielectric layer, and wherein the first, second, and fourth electrochemical cells substantially ionically isolated from one another; and
    at least two layers of dielectric material, wherein said first and second electrolytes are each disposed in a separate layer of the dielectric material.

15. The gas sensor of claim 14, wherein the second electrochemical cell is disposed askew such that the fourth and second electrodes are in fluid communication and the fifth electrode is electronically separated from the third and sixth electrodes.

16. The gas sensor of claim 15, wherein the fifth electrode is disposed in fluid communication with a reference selected from the group consisting of a vent, reference gas storage material, reference gas storage chamber, and combinations comprising at least one of the foregoing references.

17. The gas sensor of claim 15, wherein the first and seventh electrodes can fluidly communicate with an environment outside of the sensor.

18. A gas sensor for sensing $NO_x$, comprising:

a first electrochemical cell having a first electrolyte disposed between and in electrical communication with first and second electrodes;

a second electrochemical cell having a second electrolyte disposed between and in electrical communication with third and fourth electrodes;

a third electrochemical cell having said second electrolyte disposed between and in electrical communication with a fifth and said fourth electrodes wherein said first, second, and third electrochemical cells are ionically isolated from each other;

a dielectric material surrounding said first, second, and third electrochemical cells wherein said first and second electrolytes are each embedded in a separate layer of dielectric material.

19. The gas sensor of claim 18, further comprising an open gas space between said second electrode and said third electrode and fifth electrodes.

20. The gas sensor of claim 18, wherein said first and fifth electrodes are comprised of platinum, said second electrode is comprised of a gold and platinum alloy, said third electrode is comprised of a platinum alloy, and said fourth electrode is comprised of rhodium or rhodium/platinum alloy.

21. The gas sensor of claim 20, wherein said first electrochemical cell comprises an oxygen pumping cell, said second electrochemical comprises an oxygen sensing cell, and said third electrochemical cell comprises a $NO_x$ sensing cell.

* * * * *